(12) United States Patent
Schoerken et al.

(10) Patent No.: US 7,981,641 B2
(45) Date of Patent: Jul. 19, 2011

(54) PROCESSES FOR THE PRODUCTION OF TRIGLYCERIDES OF UNSATURATED FATTY ACIDS IN THE PRESENCE OF ENZYMES

(75) Inventors: Ulrich Schoerken, Duesseldorf (DE); Sabine Both, Duesseldorf (DE); Carolin Meyer, Duesseldorf (DE); Peter Horlacher, Bellenberg (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 12/061,005

(22) Filed: Apr. 2, 2008

(65) Prior Publication Data
US 2008/0182304 A1    Jul. 31, 2008

(51) Int. Cl.
$C12P\ 7/64$ (2006.01)
$C08L\ 91/00$ (2006.01)

(52) U.S. Cl. ......... 435/134; 524/313; 554/224; 554/227

(58) Field of Classification Search .................. 435/134; 524/313; 554/224, 227
See application file for complete search history.

(56) References Cited

U.S. PATENT DOCUMENTS

| | | | | |
|---|---|---|---|---|
| 5,254,722 A * | 10/1993 | Peukert et al. | ................. | 554/227 |
| 5,288,619 A | 2/1994 | Brown et al. | | |
| 5,604,119 A * | 2/1997 | Haraldsson et al. | .......... | 435/134 |
| 6,720,447 B1 * | 4/2004 | Ditrich et al. | ................. | 560/179 |
| 2003/0175914 A1 | 9/2003 | Baldenius et al. | | |
| 2005/0233427 A1 | 10/2005 | Schoerken et al. | | |
| 2010/0143486 A1 * | 6/2010 | Davar et al. | .................... | 424/497 |

FOREIGN PATENT DOCUMENTS

| | | |
|---|---|---|
| DE | 42 22 374 | 1/1994 |
| EP | 0 950 410 | 10/1999 |
| EP | 1 174 416 | 1/2002 |
| EP | 1 322 776 | 3/2002 |
| EP | 1 354 934 | 10/2003 |
| EP | 1 582 595 | 3/2005 |
| JP | 06172263 | 6/1994 |
| WO | WO 91 16443 | 10/1991 |
| WO | WO 96 37587 | 11/1996 |
| WO | WO 99 47135 | 9/1999 |
| WO | WO 00 49117 | 8/2000 |
| WO | WO 01/78531 | 10/2001 |
| WO | WO 02 24935 | 3/2002 |

OTHER PUBLICATIONS

Sodium borate. 1997. Information sheet from www.inchem.org/documents/icsc/icsc/eics0567.htm. p. 1-3.*

Borg et al., "Comparison between two processes for the enzymatic synthesis of tri-docosahexaenoylglycerol in a solvent-free medium," Biotechnology Letters, 2000, vol. 22, pp. 777-781. XP 002340871.

Castillo et al., "The Rose of Silica Gel in Lipase-Catalyzed Esterification Reactions of High-Polar Substrates", JAOCS, 1997, pp. 77-85. XP008081166.

* cited by examiner

*Primary Examiner* — Taeyoon Kim
(74) *Attorney, Agent, or Firm* — Diehl Servilla LLC

(57) ABSTRACT

Processes for the enzyme-catalyzed production of triglycerides using polyunsaturated fatty acids, in which (a) the reaction of polyunsaturated fatty acids and/or $C_{1-4}$ alkyl esters thereof with glycerol in vacuo in the presence of an immobilized enzyme to form their triglycerides is accelerated by addition of an additive from the group of weakly basic salts, complexing agents and ion exchangers and/or addition of a weakly basic salt and/or addition of an entraining agent in the form of a solvent or a gas and/or addition of glycerol-binding adsorbers and/or heat treatment of the partial glyceride intermediate product, (b) the immobilized enzymes are removed from the triglyceride by separation or filtration and (c) the remaining fatty acids and/or $C_{1-4}$ alkyl esters thereof are removed from the triglyceride by distillation, refining or extraction.

13 Claims, No Drawings

PROCESSES FOR THE PRODUCTION OF TRIGLYCERIDES OF UNSATURATED FATTY ACIDS IN THE PRESENCE OF ENZYMES

CROSS REFERENCE TO RELATED APPLICATIONS

This application claims priority under 35 U.S.C. Section 119 of U.S. Ser. No. 11/093,410 filed Mar. 30, 2005, the contents of which are incorporated by reference herein in its entirety.

BACKGROUND OF THE INVENTION

Esters of polyunsaturated fatty acids can be produced both by chemical and by enzymatic methods. Chemical syntheses have the disadvantage that very high temperatures generally have to be used and large quantities of basic catalysts are required so that secondary products and unwanted isomerizations occur to a fairly significant extent. One way of reducing the reaction temperature in the chemical synthesis of glycerol esters of polyunsaturated fatty acids was disclosed in European patent application EP 1 354 934 A1. By using a mixed catalyst of a salt of a weak acid and a strong base together with the soap of an organic $C_{2\text{-}26}$ acid, the reaction temperature was reduced to below 175° C. and preferably to 100-140° C. However, enzyme-catalyzed reactions with lipases still generally take place under milder conditions and give high-purity end products.

Thus, European patent EP 0 950 410 A1 and International patent WO 0 178 531 describe syntheses in which glycerol and free conjugated linoleic acid (CLA) are reacted with immobilized lipase at 65° C. in a vacuum of 0.01 to 0.5 torr to form CLA triglycerides. Similarly, according to European patent application EP 1174416 A1, glycerol and free CLA are reacted with lipase under reduced pressure at 70° C.

European patent application EP 1 322 776 A1 describes a lipase-catalyzed method for the production of triglycerides of polyunsaturated conjugated fatty acids from alkyl esters of the unsaturated fatty acids and glycerol which removes the alcohol formed from the reaction under reduced pressure. In addition, International patent application WO 9116443 A1 describes the esterification of glycerol and free polyunsaturated fatty acids or alkyl esters thereof to form the corresponding triglycerides by removing the water of reaction or the alcohol formed under reduced pressure.

However, enzymatic syntheses often have the disadvantage that the reactions are relatively slow.

Accordingly, the problem addressed by the invention was to improve the profitability of enzymatic processes for the production of triglycerides containing polyunsaturated fatty acids.

SUMMARY OF THE INVENTION

The present invention relates generally to fatty acid esters and, more particularly, to a new process for the enzymatic synthesis of triglycerides containing polyunsaturated fatty acids which is distinguished by an accelerated reaction.

The present invention includes a process for the enzyme-catalyzed production of triglycerides containing polyunsaturated fatty acids, in which:
(a) the reaction of polyunsaturated fatty acids and/or $C_{1\text{-}4}$ alkyl esters thereof with glycerol in vacuo in the presence of an enzyme to form their triglycerides is accelerated by addition of an additive from the group of weakly acidic salts, weakly basic salts, complexing agents, salts of complexing agents, basic and/or weakly basic ion exchangers, salts of acidic ion exchangers and/or heat treatment of the partial glyceride intermediate product,
(b) the enzymes are removed from the triglyceride by separation or filtration and
(c) the remaining fatty acids and/or esters thereof are removed from the triglyceride by distillation, refining or extraction.

It has surprisingly been found that the reaction of polyunsaturated fatty acids and/or esters thereof with glycerol to form triglycerides can be significantly accelerated by synthesis in vacuo in the additional presence of an additive, entraining agent or glycerol-binding adsorber or by heat treatment of the partial glycerides occurring as intermediate product in the synthesis. The auxiliaries used in addition to the vacuum lead to a significant reduction in the reaction times. Compared with the chemical synthesis of triglycerides of polyunsaturated fatty acids, the reaction can be carried out at much lower temperatures which leads to a reduction in unwanted secondary products, such as unwanted isomers for example. The reaction rate of this enzymatic process is normally very low. However, the process according to the invention leads to a reduction in the reaction time and thus makes the enzymatic process a profitable process.

DETAILED DESCRIPTION OF THE INVENTION

The process is applicable to linear unsaturated fatty acids containing more than one double bond and/or $C_{1\text{-}4}$ alkyl esters, preferably methyl and/or ethyl esters, thereof selected from the group consisting of naturally occurring polyunsaturated and polyconjugated unsaturated fatty acids and conjugated linoleic and linolenic acids. Docosahexaenoic acid, eicosapentaenoic acid, arachidonic acid, γ-linolenic acid and conjugated linoleic acid are preferably use, the c9,t11 and t10,c12 isomers of conjugated linoleic acid (CLA) and esters thereof being particularly preferred. The concentration range selected for the raw materials used is from 3 to 6 mol fatty acid or ester to 1 mol glycerol, 3.2 to 4.0 mol fatty acid or ester to 1 mol glycerol preferably being used to achieve an optimal reaction rate.

Typical examples of suitable enzymes, which are not intended to limit the invention in any way, are lipases, phospholipases and/or esterases of microorganisms selected from the group consisting of *Alcaligenes, Aspergillus, Candida, Chromobacterium, Rhizomucor, Penicilium, Pseudomonas, Rhizopus, Thermomyces, Geotrichum, Mucor, Burkholderia* and mixtures thereof. Lipases and esterases from the organisms *Candida, Rhizomucor* and *Rhizopus* are preferred because they are particularly active. *Candida antarctica* B and *Rhizomucor miehei* are particularly preferred. The lipases, phospholipases or esterases selected are preferably used immobilized on a carrier. Lipases immobilized on carrier material are particularly suitable, more especially 3 to 12% by weight of immobilizate, based on the percentage fat content.

The temperature range suitable for the reaction is determined by the optimum activity of the enzymes. Temperatures in the range from 40 to 90° C. have proved to be particularly suitable for the lipases preferably selected, temperatures in the range from 55 to 80° C. being preferred. A vacuum of at least 200 mbar, preferably 1 to 100 mbar and more preferably 20 to 60 mbar should be applied. The preferred process parameters are determined by the acceleration to be achieved in the reaction rate.

Now, it has surprisingly been found that the reaction can be significantly accelerated by addition of certain additives, such as weakly basic ion exchangers, salts of a complexing agent, salts of a weak acid and salts of acidic ion exchangers. Sodium and potassium salts of carbonates, citrates, acetates and phosphates, above all sodium carbonate, have proved to be particularly suitable for this purpose. All the additives are added to the reaction mixture in the form of a solution or suspension in a little water at the beginning of the reaction. Ion exchangers may be added without preliminary suspension. The reaction takes place optimally in a concentration range of 0.01 to 5% by weight of the additives, based on the weight of the fatty acid or alkyl ester component. In the case of the salts, the preferred range is from 0.05 to 2% by weight while the particularly preferred range is from 0.01 to 1% by weight.

Entraining agents, such as gases or solvents, are also used to accelerate the reaction. Inert gases or solvents which form an azeotropic mixture with water or short-chain alcohols are particularly suitable. It has been found that nitrogen in particular leads to optimized reaction conditions. All entraining agents are continuously added to the reaction mixture and are removed therefrom at the same rate under a vacuum. If the use of an entraining agent is combined with the use of an additive, such as for example a weakly basic salt, such as sodium carbonate with nitrogen as entraining agent, synergistic effects can be observed and an optimized reaction in terms of reaction rate and yield can be achieved. Accordingly, these two methods are preferably used in the enzyme-catalyzed production of triglycerides containing polyunsaturated fatty acids.

Influencing of the reaction equilibrium, which also leads to acceleration of the reaction, can also be effected by addition of glycerol-binding adsorbers. Hydrophilic polymers, such as silica gel powder for example, have proved to be suitable for this purpose.

In addition, it has surprisingly been found that heat treatment of the partial glyceride formed as intermediate product during the reaction is another reaction-accelerating measure. To this end, the partial glyceride is heated to a temperature of 80 to 160° C. and preferably to a temperature of 90 to 120° C. after removal of the immobilized enzymes by filtration.

After the reaction, the immobilized enzymes are removed by separation or filtration and the unreacted fatty acids or alkyl esters thereof are removed by refining or distillation, preferably short-path distillation.

The present invention will now be illustrated in more detail by reference to the following specific, non-limiting examples.

EXAMPLES

Production of Triglycerides of Conjugated Linoleic Acid

Example 1

Lipase Screening for the Synthesis of Triglycerides:

Various lipases (see Table 1, batches 1 to 9) were immobilized in 9 bottles. To this end, equal quantities of the enzyme preparation and the adsorber resin Amberlite XAD 16 (Rohm & Haas) were shaken overnight at 30° C. in 10 times the quantity of water. The immobilized enzymes were then filtered off and dried overnight on a paper filter.

In 12 bottles, various immobilized lipases (see Table 1, batches 1-12; batches 1-9 are the lipases immobilized on Amberlite, batches 10-12 are lipase immobilizates produced by the manufacturer) were tested for their ability to synthesize glycerides. To this end, 0.75 g of CLA fatty acid, 0.07 g of glycerol, 2.5 g of t-butanol, 0.5 g of molecular sieve and 0.15 g of each immobilized lipase were weighed in. The closed bottles were incubated for 48 hours at 45° C. on a shaker operating at 200 r.p.m. The content of glycerides formed was analyzed by gas chromatography and evaluated via the peak area.

An analogous test with the same composition was carried out at 60° C. The 12 closed bottles were incubated for 48 hours at 60° C. on a shaker operating at 200 r.p.m.

The content of glycerides formed was analyzed by gas chromatography and evaluated via the peak area.

In addition, stirred batches were prepared without the use of t-butanol. To this end, 0.75 g of CLA fatty acid, 0.07 g of glycerol, 0.5 g of molecular sieve and 0.15 g of the immobilized lipase were weighed into 12 bottles. The closed bottles were immobilized for 48 hours at 40° C. while stirring with magnetic stirring rods. The content of glycerides formed was analyzed by gas chromatography and evaluated via the peak area.

Results:

The result is expressed as the maximum glyceride content achieved. Analyses were conducted after 24 hours and 48 hours.

A: incubation shaken at 45° C.
B: incubation shaken at 60° C.
C: incubation shaken at 40° C.

TABLE 1

Enzymatic preparation of triglycerides of CLA using various immobilized lipases.

| Batch | Lipase | Manufacturer | Organism | Glycerides % Test A | Glycerides % Test B | Glycerides % Test C |
|---|---|---|---|---|---|---|
| 1 | Chirazym L 10 | Roche | Alcaligenes sp. | 0% | 22.2% | 21.3% |
| 2 | Lipase A | Amano | Aspergillus niger | 1.1% | 0.5% | 0.6% |
| 3 | Novocor ADL | Novozymes | Candida antarctica A | 0% | 26.7% | 26.8% |
| 4 | Lipomod 34 | Biocatalysts | Candida cylidracea | 21.9% | 9.2% | 9.1% |
| 5 | Lipase AY | Amano | Candida rugosa | 0% | 22.5% | 21.4% |
| 6 | Lipase L115 | Biocatalysts | Porcine pancreas | 0% | 0% | 0% |
| 7 | Lipase R | Amano | Penicilium roquefortii | 1.5% | 0% | 0% |
| 8 | Lipase PS | Amano | Pseudomonas cepacia | 0% | 2.5% | 0% |
| 9 | Lipase F-AP 15 | Amano | Rhizopus oryzae | 60.4% | 61.6% | 45.0% |
| 10 | Novozym 435 | Novozymes | Candida antarctica B | 63.1% | 74.1% | 63.1% |

TABLE 1-continued

Enzymatic preparation of triglycerides of CLA using various immobilized lipases.

| Batch | Lipase | Manufacturer | Organism | Glycerides % Test A | Glycerides % Test B | Glycerides % Test C |
|---|---|---|---|---|---|---|
| 11 | Lipozym RM IM | Novozymes | Rhizomucor miehei | 47.3% | 47.8% | 42.1% |
| 12 | Lipozym TL IM | Novozymes | Thermomyces lanugenosus | 41.9% | 13.3% | 10.3% |

Most of the lipases are capable of forming glycerides under the selected reaction conditions. Differences in the synthesis performance of the lipases can also arise through the differences in the unit activities of the enzyme preparations. Novozym 435 has proved to be the preferred enzyme for the desired reaction.

Example 2

Influence of Basic Salts on the Reaction of CLA-free Acid with Glycerol:

Glycerol (2.5 g) and CLA fatty acid (27.5 g) were weighed into 8 flasks in a molar ratio of 1:3.6. 0.33% by weight of various salts suspended in the same quantity of water (see Table below) were added to the batches. After addition of 1.25 g of immobilized *Candida antarctica* B lipase (lipase from Novozymes, Denmark), a vacuum of 20 mbar was applied while stirring with a magnetic stirring fish at a temperature of 60° C. After 17 hours, a sample of the oil phase was removed and the content of reacted CLA fatty acid was determined by determination of the acid value. The starting acid value was 181.

Results

TABLE 2

Acceleration of the reaction of free CLA to CLA triglycerides, as measured from the acid value as a function of the salt added

| Batch | Salt | Acid value |
|---|---|---|
| 1 | Blank | 100 |
| 2 | Sodium chloride | 132 |
| 3 | Sodium carbonate | 46 |
| 4 | Sodium citrate | 70 |
| 5 | Sodium acetate | 53 |
| 6 | Sodium phosphate | 64 |
| 7 | Sodium tartrate | 113 |
| 8 | Sodium tetraborate | 101 |

The results show that sodium carbonate, citrate, acetate and phosphate clearly accelerate the synthesis of CLA triglyceride from the free acid, the best results being achieved with sodium carbonate.

Example 3

Dependence of Reaction Rate on the Sodium Carbonate Concentration Added

Glycerol (9 g) and CLA fatty acid (100 g) were weighed into 3 flasks in a molar ratio of 1:3.7. 0.1% sodium carbonate suspended in the same quantity of water was added to batch 2, 1% of sodium carbonate suspended in the same quantity of water was added to batch 3. After addition of 7 g of immobilized *Candida antarctica* B lipase, a vacuum of 20 mbar was applied while stirring with a magnetic stirring fish at a temperature of 60° C. Samples of the oil phase were removed after 24 and 48 hours and the content of CLA glycerides formed was determined by gas chromatography. The result is expressed as the percentage triglyceride content, based on the sum of di- and triglyceride formed.

Results

TABLE 3

Acceleration of the reaction of free CLA to CLA triglycerides, as measured from the percentage triglyceride content - based on the sum of di- and triglyceride formed - as a function of the sodium carbonate concentration added

| Batch | Sodium carbonate conc. | 24 h | 48 h |
|---|---|---|---|
| 1 | None | 41% | 63% |
| 2 | 0.1% by weight | 76% | 94% |
| 3 | 1.0% by weight | 63% | 91% |

Sodium carbonate has a reaction-accelerating effect, particularly in a concentration range of 0.1% by weight to 1.0% by weight.

Example 4

Influence of Complexing Agents on the Reaction of CLA-free Acid with Glycerol

Glycerol (5 g) and CLA fatty acid (55 g) were weighed into 5 flasks in a molar ratio of 1:3.6. 0.42% by weight of various complexing agents suspended in the same quantity of water (see Table below) was added to the batches. After addition of 2.5 g of immobilized *Candida antarctica* B lipase, a vacuum of 20 mbar was applied while stirring with a magnetic stirring fish at a temperature of 60° C. A sample of the oil phase was removed after 17 hours and the content of reacted CLA fatty acid was determined by determination of the acid value. The starting acid value was 181.

Results

TABLE 4

Acceleration of the reaction of free CLA to CLA triglycerides, as measured from the acid value as a function of the complexing agent added

| Batch | Salt | Acid value |
|---|---|---|
| 1 | Blank | 86 |
| 2 | EDTA free acid | 79 |
| 3 | EDTA disodium salt | 76 |
| 4 | EDTA tetrasodium salt | 57 |
| 5 | Trinitriloacetic acid trisodium salt | 48 |

The complexing agents completely present in salt form in particular accelerate the synthesis of CLA triglyceride from the free acid.

Example 5
Influence of Ion Exchangers on the Reaction of CLA-free Acid with Glycerol Glycerol (5 g) and CLA fatty acid (55 g) were weighed into 8 flasks in a molar ratio of 1:3.6. 3.3% by weight of various ion exchangers (see Table below) were added to the batches. After addition of 2.5 g of immobilized *Candida antarctica* B lipase, a vacuum of 20 mbar was applied while sing with a magnetic stirring fish at a temperature of 60° C. A sample of the oil phase was removed after 25 hours and the content of CLA glycerides formed was determined by gas chromatography. The result is expressed as the percentage triglyceride content, based on the sum of di- and triglyceride formed.
Results

TABLE 5

Acceleration of the reaction of free CLA to CLA triglycerides, as measured from the quantity of triglyceride as a function of the ion exchanger added

| Batch | Salt | Triglyceride [% by wt.] |
|---|---|---|
| 1 | Blank | 22 |
| 2 | Lewatit TP-260, sodium form | 58 |
| 3 | Amberlite IRC-748, sodium form | 49 |
| 4 | Lewatit MP-62, free base | 41 |
| 5 | Dowex MSC-1, free acid | 0 |
| 6 | Lewatit TP-207, sodium form | 65 |
| 7 | Dowex 66, free base | 41 |
| 8 | Duolite C433, free acid | 0 |

The results show that weakly basic ion exchangers and acidic or completing resins in their salt form accelerate the synthesis of CLA triglyceride from the free acid. By contrast, acidic ion exchangers inhibit the triglyceride synthesis.

Example 6

Influence of Nitrogen Blanketing on the Reaction of CLA-free Acid with Glycerol

Glycerol (10.9 g) and CLA fatty acid (100 g) were weighed into 2 flasks in a molar ratio of 1:3.0. After addition of 5 g of immobilized *Candida antarctica* B lipase, a vacuum of 20 mbar was applied while stirring with a magnetic stirring fish at a temperature of 60° C. One batch was continuously blanketed with nitrogen. Samples of the oil phase were removed after 24, 72 and 96 hours and the content of CLA glycerides formed was determined by gas chromatography. The result is expressed as the percentage triglyceride content, based on the sum of di- and triglyceride formed. In addition, the acid value was determined at the times mentioned. The starting acid value was 179.
Results

TABLE 6

Acceleration of the reaction of free CLA to CLA triglycerides, as measured from the triglyceride content and the acid value as a function of the entraining agent nitrogen

| Batch | 24 h | 72 h | 96 h |
|---|---|---|---|
| | Triglyceride content | | |
| 1 (Without nitrogen) | 13% | 53% | 63% |
| 2 (With nitrogen) | 8% | 69% | 81% |
| | Acid value | | |
| 1 (Without nitrogen) | 51 | 25 | 16 |
| 2 (With nitrogen) | 52 | 8 | 2 |

Blanketing with nitrogen increases the reaction rate in the synthesis of triglycerides from free fatty acid, particularly in the second half of the reaction.

Example 7

Synergistic Effect of Nitrogen Blanketing and Basic Additive on the Reaction of CLA-free Acid Glycerol (5 g) and CLA fatty acid (55 g) were weighed into 4 flasks in a molar ratio of 1:3.6. 0.36% by weight of sodium acetate suspended in the same quantity of water was added to batches 3 and 4. After addition of 3.0 g of immobilized *Candida antarctica* B lipase, a vacuum of 60 mbar was applied while stirring with a magnetic stirring fish at a temperature of 60° C. Batches 2 and 4 were continuously blanketed with nitrogen. Samples of the oil phase were removed after 24 hours and the content of CLA glycerides formed was determined by gas chromatography.
Results

TABLE 7

Acceleration of the reaction of free CLA to CLA triglycerides, as measured from the triglyceride content as a function of the entraining agent nitrogen and in the presence of sodium carbonate

| Batch | Nitrogen | Sodium acetate | Fatty acid | Mono-glyceride | Diglyceride | Triglyceride |
|---|---|---|---|---|---|---|
| 1 | No | No | 63.4% | 12.4% | 24.5% | 0.0% |
| 2 | Yes | No | 58.8% | 11.9% | 29.5% | 0.0% |
| 3 | No | Yes | 48.7% | 3.9% | 39.8% | 7.8% |
| 4 | Yes | Yes | 46.1% | 1.2% | 30.4% | 22.5% |

These results also prove that blanketing with nitrogen significantly increases the reaction rate in the synthesis of triglyceride from free fatty acid. Basic additive and blanketing with nitrogen produce a synergistic effects. The effect of nitrogen blanketing in addition to the vacuum applied is greater in the presence of a basic additive.

Example 8

Influence of the Solvent 2-methyl-2-butanol as Entraining Agent on the Reaction of CLA-free Acid with Glycerol Glycerol (4 g) and CLA-free acid (50 g) were weighed into 2 flasks in a molar ratio of 1:4.1. After addition of 3 g of Novozym 435, a vacuum of 60 mbar was applied while stirring with a magnetic stirring fish at a temperature of 60° C. 2-Methyl-2-butanol was continuously pumped into one batch at a flow rate of 0.05 ml/min., evaporating from the batch under the vacuum applied. Samples of the oil phase were removed after 18 hours and the content of CLA glycerides formed was determined by gas chromatography. The result is expressed as the percentage triglyceride content, based on the sum of di- and triglyceride formed.

Results

TABLE 8

Acceleration of the reaction of free CLA to CLA triglycerides, as measured from the triglyceride content as a function of the entraining agent 2-methyl-2-butanol

| Batch | 18 h |
|---|---|
| Triglyceride content | |
| 1 (Without 2-methyl-2-butanol) | 34% |
| 2 (With 2-methyl-2-butanol) | 56% |

The use of 2-methyl-2-butanol as entraining agent increases the reaction rate in the synthesis of triglyceride from CA-free acid.

Example 9

Influence of Nitrogen Blanketing on the Reaction of CLA Ethyl Ester with Glycerol in the Presence of Sodium Carbonate Glycerol (5 g) and CLA ethyl ester (60 g) were weighed into 2 flasks in a molar ratio of 1:3.6. 0.15% by weight of sodium carbonate suspended in the same quantity of water (see Table below) were added to the batches. After addition of 2.5 g of immobilized *Candida antarctica* B lipase, a vacuum of 20 mbar was applied while stirring with a magnetic stirring fish at a temperature of 60° C. One batch was continuously blanketed with nitrogen. Samples of the oil phase were removed after 16, 40 and 63 hours and the content of CLA glycerides formed was determined by gas chromatography. The result is expressed as the percentage triglyceride content, based on the sum of di- and triglyceride formed.
Results

TABLE 9

Acceleration of the reaction of CLA ethyl ester with glycerol to CLA triglycerides in the presence of sodium carbonate, as measured from the triglyceride content - based on the sum of di- and triglyceride formed - as a function of the blanketing with nitrogen

| Batch | 16 h | 40 h | 63 h |
|---|---|---|---|
| Triglyceride content [% by wt.] | | | |
| 1 (Without nitrogen) | 17 | 20 | 21 |
| 2 (With nitrogen) | 36 | 65 | 77 |

Blanketing with nitrogen increases the reaction rate in the synthesis of triglyceride from CLA ethyl ester over the entire course of the reaction. Without the entraining agent nitrogen, the reaction is very slow.

Example 10

Influence of Adding Cyclohexane on the Reaction of CLA Methyl Ester with Glycerol Glycerol (11 g) and CLA methyl ester (120 g) were weighed into 2 flasks in a molar ratio of 1:3.6. After addition of 6 g of immobilized *Candida antarctica* B lipase, a vacuum of 120 mbar was applied while stirring with a magnetic stirring fish at an internal temperature of 50° C. in batch 1 and at an internal temperature of 55-60° C. in batch 2. Cyclohexane was continuously added to both batches at a flow rate of 0.1 ml/min. Samples of the oil phase were removed after 20, 48 and 72 h and the content of CLA glycerides formed was determined by gas chromatography. The result is expressed as the percentage triglyceride content, based on the sum of di- and triglyceride formed.
Results

TABLE 10

Acceleration of the reaction of CLA methyl ester with glycerol to CLA triglycerides, as measured from the triglyceride content - based on the sum of di- and triglyceride formed - as a function of the addition of cyclohexane as entraining agent

| Batch | 16 h | 40 h | 63 h |
|---|---|---|---|
| Triglyceride content [% by wt.] | | | |
| 1 (50° C. internal) | 34 | 56 | 77 |
| 2 (55-60° C. internal) | 50 | 71 | 82 |

The addition of cyclohexane promotes the formation of CLA triglyceride. In addition, increasing the internal temperature from 50° C. to 55-60° C. improves the formation of triglycerides.

Example 11

Reaction Acceleration by Heat Treatment of the Partial Glyceride Intermediate Product in the Synthesis of CLA Triglycerides Glycerol (25 g) and CLA methyl ester (275 g) were weighed into a flask in a molar ratio of 1:3.4. 0.33% of sodium carbonate suspended in the same quantity of water was then added. After addition of 12.5 g of immobilized *Candida antarctica* B lipase, a vacuum of 20 mbar was applied while stirring with a magnetic stirring fish at a temperature of 60° C. After a reaction time of 5 hours, the immobilized enzyme was removed by filtration. The batch was analyzed for its glyceride distribution by gas chromatography and then divided into 4×50 g batches. After a reaction time of 5 hours, no CLA triglyceride had been formed and the percentage content of diglycerides, based on the total glyceride content, was 92%. The first batch was not treated. The second batch was heated for 30 mins. to 120° C. The third batch was heated for 30 mins. to 80° C. after the addition of 2% by weight of Lewatit S 100. The fourth batch was heated for 30 mins. to 80° C. after the addition of 0.2% by weight of iron(II) chloride. After the heating, Lewatit and iron chloride were removed from batches 3 and 4 by filtration. 3 g of immobilized *Candida antarctica* B lipase were added to each of the batches and a vacuum of 20 mbar was applied while stirring with a magnetic stirring fish at a temperature of 60° C. Samples of the oil phase were removed after 16 hours and the content of CLA glycerides formed was determined by gas chromatography. The result is expressed as the percentage triglyceride content based on the sum of di- and triglyceride formed.
Results

TABLE 11

Acceleration of the reaction of CLA methyl ester with glycerol to CLA triglycerides, as measured from the triglyceride content after 16 h - based on the sum of di- and triglyceride formed - by heat treatment of the partial glyceride intermediate product in the synthesis of CLA triglycerides

| Batch | Treatment | TG content after 16 h |
|---|---|---|
| 1 | Blank | 34% |
| 2 | 30 mins. at 120° C. | 51% |

TABLE 11-continued

Acceleration of the reaction of CLA methyl ester with glycerol to CLA triglycerides, as measured from the triglyceride content after 16 h - based on the sum of di- and triglyceride formed - by heat treatment of the partial glyceride intermediate product in the synthesis of CLA triglycerides

| Batch | Treatment | TG content after 16 h |
|---|---|---|
| 3 | 2% Lewatit S 100, 30 mins. at 80° C. | 48% |
| 4 | 0.2% iron chloride, 30 mins. at 80° C. | 55% |

An interim treatment of the diglyceride formed results in a faster synthesis of CLA triglyceride. The interim treatment probably catalyzes an acyl migration from the 1,3-diglyceride mainly formed to 1,2-diglyceride which can be enzymatically esterified at a faster rate.

Example 12

Enzyme-stabilizing Properties of Silica Gel Powder in Low-water Lipase-catalyzed Reactions in the Presence of Glycerol The stabilizing effect on *Candida antarctica* B lipase is illustrated with reference to the glycerololysis of sunflower oil to the corresponding monoglyceride over a period of 48 days. To this end, 2 bottles were filled with 10 g of sunflower oil, 6 g of glycerol and 7.5 g of t-butanol. 2 g silica gel powder were also added to batch 2. After addition of 1.5 g of immobilized *Candida* B lipase, the batches were incubated on a shaker at 45° C. A sample is removed after 24 hours and analyzed for its glyceride distribution. 8 Re-uses were made of the two batches over a period of 48 days, the immobilizate being removed from the rest of the batch by filtration and re-added to the next batch. After 48 days, a sample was removed from the eighth batch after 24 hours and analyzed for its glyceride distribution. The result is expressed as the ratio of mono- to di- and triglyceride.

TABLE 12

Acceleration of the reaction of sunflower oil with glycerol, as measured from the glyceride distribution as a function of the addition of the glycerol-binding adsorber silica gel powder

| Batch | Reaction time | Monoglyceride | Diglyceride | Triglyceride |
|---|---|---|---|---|
| 1 | 1 day | 80% | 20% | 0% |
| 1 | 48 days | 60% | 15% | 25% |
| 2 | 1 day | 80% | 20% | 0% |
| 2 | 48 days | 83% | 17% | 0% |

The addition of silica gel powder stabilizes *Candida antarctica* B lipase in a low-water medium in the presence of glycerol excesses.

Other tests showed that the glycerol concentration in particular has an influence on deactivation of the lipase. Silica gel is capable of adsorbing glycerol, thereby reducing the concentration of glycerol in the liquid phase.

Example 13

Reaction of CLA-free Acid with Glycerol and Working-up of the Product by Refining Glycerol (21.8 g) and CLA-free acid (210 g) were weighed into 2 flasks in a molar ratio of 1:3.16. After addition of 15 g of Lipozym RM 1M to batch 1 and 15 g of immobilized *Candida antarctica* B lipase to batch 2, a vacuum of 20 mbar was applied while stirring with a magnetic stirring fish at a temperature of 60° C. The batches were continuously purged with nitrogen. The synthesis of batch 1 is terminated after 96 hours and the synthesis of batch 2 is terminated after 92 hours and the immobilized enzymes were removed by filtration. The two batches were refined with sodium silicate. To this end, 2% by weight of sodium silicate were added to the batches which were then stirred for 1 hour at 60° C. The suspension was then filtered through a paper filter. Samples of the oil phase were removed before and after refining and the content of CLA glycerides formed was determined by gas chromatography. The result is expressed as the percentage triglyceride content based on the sum of di- and triglyceride formed. Additional samples were taken before and after refining and analyzed for their acid value.

TABLE 13

Acceleration of the reaction of free CLA to CLA triglycerides, as measured from the percentage triglyceride content - based on the sum of di- and triglyceride formed - and from the acid value before and after refining

| Batch | Acid value Before/after refining | Triglyceride Before/after refining |
|---|---|---|
| 1 | 12.3/1.5 | 96%/96% |
| 2 | 2.8/2.1 | 93%/93% |

The content of free CLA fatty acid in the CLA triglyceride can be reduced by refining without degradation of the CLA triglyceride.

Example 14

Reaction of CLA Methyl Ester with Glycerol and Working-up of the Product by Distillation Raw Materials Used:

| Glycerol (99.9%): | 2.9 kg |
|---|---|
| CLA methyl ester: | 34.5 kg |
| Enzyme (Novozym 435): | 1.3 kg |

Apparatus:

60 liter stirred vessel with heater, temperature control, vacuum connection incl. control and pump The materials used were introduced with stirring into the stirred vessel and the reaction was started (reaction conditions: 60° C. internal temperature, 50 mbar vacuum). After a reaction time of 48 h, 47.9% of triglycerides had been formed in the reaction mixture and were purified by short-path distillation.

Conditions:

Short-path Distillation, One-step:

| Temperature, feed: | 80° C. |
|---|---|
| Temperature, evaporator: | 190° C. |
| Temperature, cooling finger: | 40° C. |
| Flow: | 200 ml/h |
| Vacuum: | <0.5 mbar |

73.9% of triglycerides were obtained on termination of distillation.

Example 15

Reaction of CLA Ethyl Ester with Glycerol and Working-up of the Product by Distillation
Raw Materials Used:

| | |
|---|---|
| Glycerol (99.9%): | 2.9 kg |
| CLA ethyl ester: | 35.5 kg |
| Enzyme (Novozym 435 from Novozymes): | 1.3 kg |

Apparatus:
60 liter stirred vessel with heater, temperature control, vacuum connection incl. control and pump The materials used were introduced with stirring into the stirred vessel and the reaction was started (reaction conditions: 60° C. internal temperature, 5 mbar vacuum). After a reaction time of 72 h, 62.1% of triglycerides had been formed in the reaction mixture and were purified by short-path distillation.
Conditions:
Short-path Distillation of the Fatty Acids, One-step:

| | |
|---|---|
| Temperature, feed: | 80° C. |
| Temperature, evaporator: | 190° C. |
| Temperature, cooling finger: | 40° C. |
| Flow: | 200 ml/h |
| Vacuum: | <0.5 mbar |

73.9% of triglycerides were obtained on termination of distillation.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process for enzyme-catalyzed production of triglycerides comprising:
   (a) reacting one or more polyunsaturated fatty acids and/or $C_{1-4}$ alkyl esters thereof with glycerol in vacuo in the presence of at least one enzyme to form triglyceride and at least one partial glyceride intermediate product, wherein the reaction is accelerated by addition of at least one additive, wherein the additive is selected from the group consisting of weakly basic salts, complexing agents, and salts of acidic ion exchangers;
   (b) removing the enzyme from the triglyceride; and
   (c) removing remaining fatty acids and/or $C_{1-4}$ alkyl esters thereof from the triglyceride,
   wherein the enzyme is selected from the group consisting of lipases, phospholipases, and esterases;
   wherein the weakly basic salt is selected from the group consisting of sodium carbonate, sodium citrate, sodium acetate, sodium phosphate, potassium carbonate, potassium citrate, potassium acetate, and potassium phosphate; and
   wherein the complexing agent is selected from the group consisting of EDTA free acid, EDTA disodium salt, EDTA tetrasodium salt, and trinitriloacetic acid trisodium salt.

2. The process according to claim 1, wherein the one or more polyunsaturated fatty acids and/or $C_{1-4}$ alkyl esters thereof comprises a compound selected from the group consisting of docosahexaenoic acid, eicosapentaenoic acid, arachidonic acid, y-linolenic acid, linoleic acid, conjugated linoleic acid, and $C_{1-4}$ alkyl esters thereof.

3. The process according to claim 1, wherein the enzyme is immobilized on a carrier.

4. The process according to claim 1, wherein the reaction is carried out under a pressure of 200 mbar or less.

5. The process according to claim 1, wherein the enzyme is removed from the triglyceride by separation or filtration.

6. The process according to claim 1, wherein the remaining fatty acids and/or $C_{1-4}$ alkyl esters thereof are removed from the triglyceride by distillation, refining, or extraction.

7. The process according to claim 1, wherein the additive is present in an amount of from 0.001 to 5% by weight.

8. The process of claim 1 which comprises: after step (a),
   (1) separating the enzyme from the product mixture to form a separated product mixture;
   (2) heating the separated product mixture at a temperature of from 80° C. to 160° C. to form a heat-treated separated product mixture;
   (3) introducing an enzyme into the heat-treated product mixture;
   (4) heating the heat-treated product mixture containing the enzyme, whereby the amount of triglyceride formed is increased; and
   (b) separating the triglyceride from the heat-treated product mixture.

9. A process for enzyme-catalyzed production of triglycerides comprising polyunsaturated fatty acids, comprising:
   (a) reacting one or more polyunsaturated fatty acids and/or $C_{1-4}$ alkyl esters thereof with glycerol in vacuo in the presence of at least one enzyme to form triglyceride and at least one partial glyceride intermediate product, wherein the reaction is accelerated by addition of at least one additive selected from the group consisting of weakly basic salts, complexing agents, and salts of acidic ion exchangers; wherein the reaction further comprises:
      (i) addition of at least one entraining agent in the form of a solvent which forms azeotropes with water or short-chain alcohols; and/or
      (ii) heat treatment of the partial glyceride intermediate product;
   (b) removing the enzyme from the triglyceride by separation or filtration; and
   (c) removing the remaining fatty acids and/or $C_{1-4}$ alkyl esters thereof from the triglyceride by distillation, refining or extraction,
   wherein the enzyme is selected from the group consisting of lipases, phospholipases, and esterases;
   wherein the weakly basic salt is selected from the group consisting of sodium carbonate, sodium citrate, sodium acetate, sodium phosphate, potassium carbonate, potassium citrate, potassium acetate, and potassium phosphate; and
   wherein the complexing agent is selected from the group consisting of EDTA free acid, EDTA disodium salt, EDTA tetrasodium salt, and trinitriloacetic acid trisodium salt.

10. The process according to claim 1, wherein the reaction of step (a) further comprises the addition of at least one entraining agent selected from the group consisting of nitrogen, 2-methyl-2-butanol, and cyclohexane.

11. The process according to claim 10, wherein the entraining agent is in the form of a solvent which forms azeotropes with water or short-chain alcohols.

12. The process according to claim 10, wherein the entraining agent is present in an amount of from 0.001 to 5% by weight.

13. The process according to claim 1, wherein the reaction of step (a) further comprises heat treatment of the partial glyceride intermediate product.

* * * * *